United States Patent [19]
Tritsch

[11] 3,954,106
[45] May 4, 1976

[54] DISPOSABLE DIAPER HAVING AN OFF-SET TAB FASTENER MEANS AND RELEASE FACING ON DIAPER OUTER SURFACE

[75] Inventor: Ludwig Tritsch, Wilmette, Ill.

[73] Assignee: Johnson & Johnson, New Brunswick, N.J.

[22] Filed: Jan. 8, 1975

[21] Appl. No.: 539,486

[52] U.S. Cl. .................................. 128/287; 128/284
[51] Int. Cl.² ................... A41B 13/02; A61F 13/16
[58] Field of Search ............ 128/284, 286, 287, 290

[56] References Cited
UNITED STATES PATENTS

| | | | |
|---|---|---|---|
| 3,620,217 | 11/1971 | Gellert | 128/284 |
| 3,630,201 | 12/1971 | Endres | 128/287 |
| 3,638,651 | 2/1972 | Torr | 128/284 |
| 3,794,038 | 2/1974 | Buell | 128/287 |
| 3,840,013 | 10/1974 | Mesek et al. | 128/284 |
| 3,848,597 | 11/1974 | Endres | 128/287 |

Primary Examiner—Aldrich F. Medbery

[57] ABSTRACT

A disposable diaper having a moisture-impermeable backing sheet and an absorbent pad superposed on the backing sheet is provided with adhesive tap-type fasteners which do not require a separate release sheet for protecting the adhesive surfaces thereof. Each fastener is secured to the backing sheet and comprises a fixed end attached to the outer surface of the backing sheet and a free working end removably attached to an outwardly-facing release region provided on the backing sheet.

3 Claims, 4 Drawing Figures

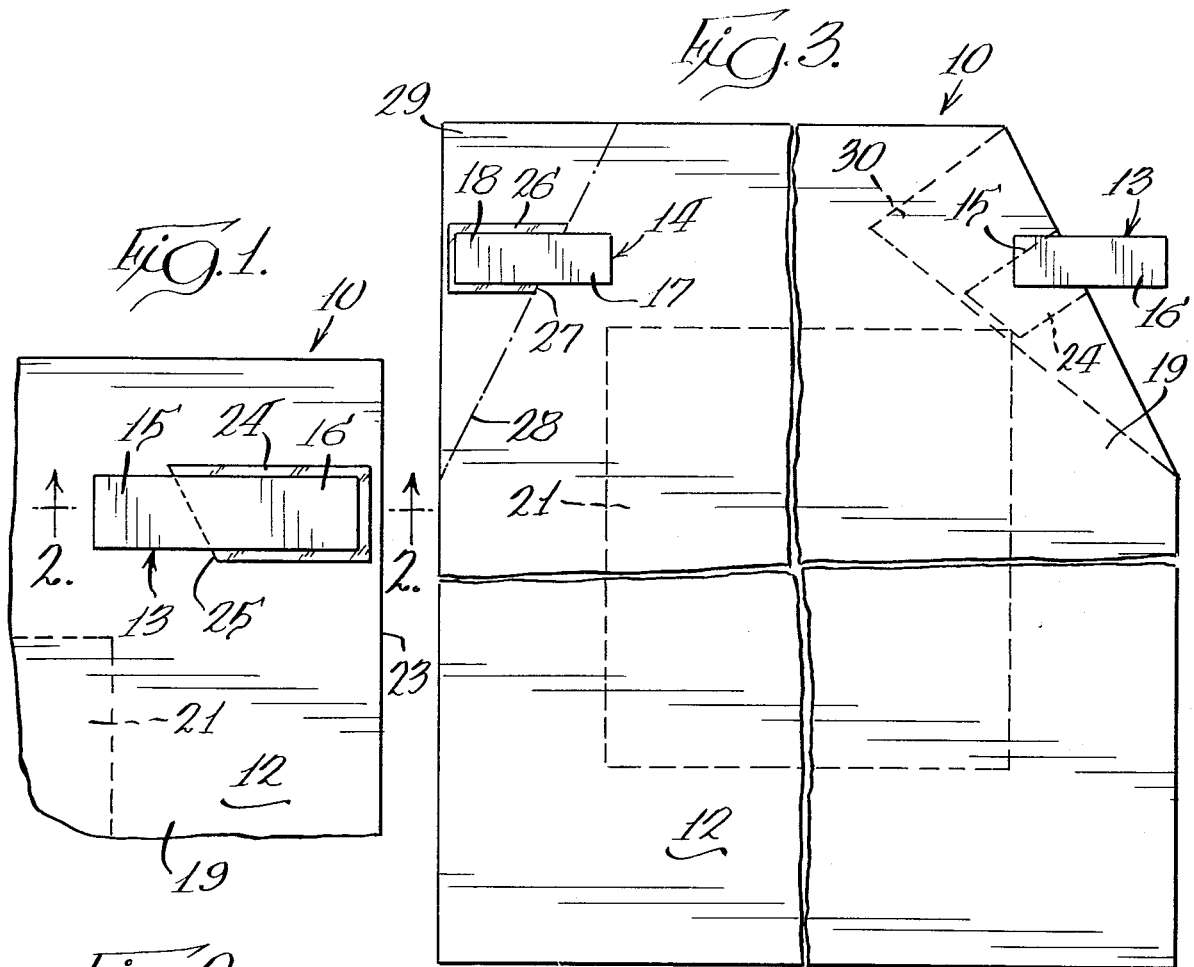
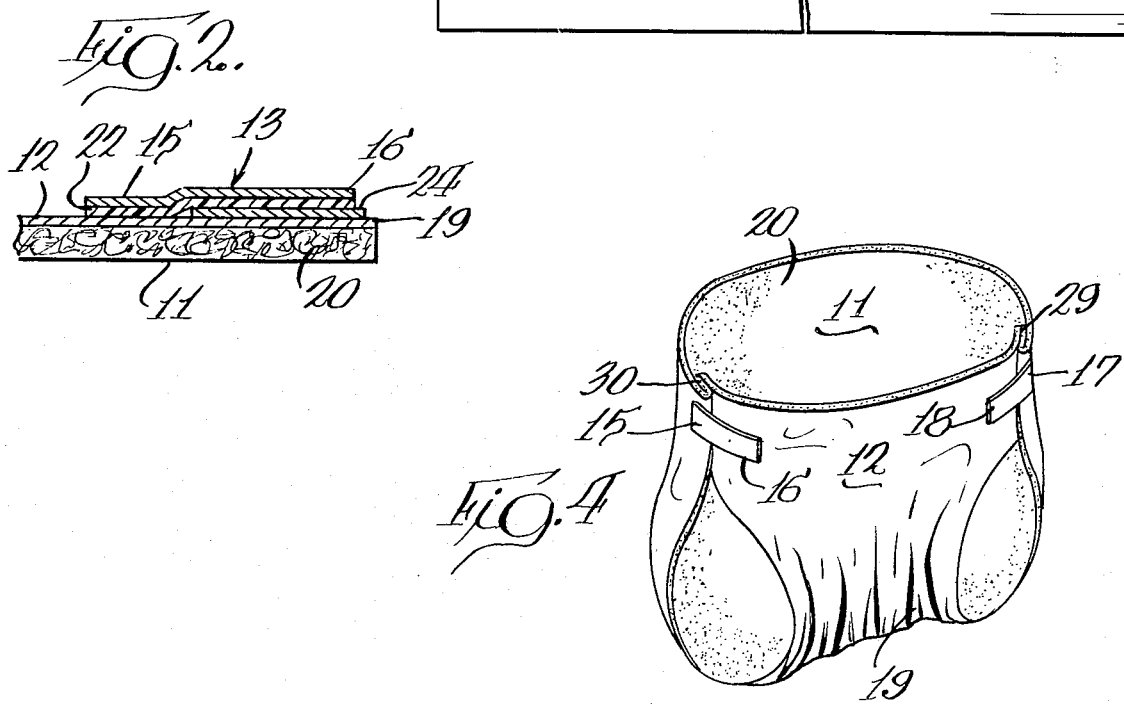

DISPOSABLE DIAPER HAVING AN OFF-SET TAB FASTENER MEANS AND RELEASE FACING ON DIAPER OUTER SURFACE

BACKGROUND OF THE INVENTION

This invention relates to disposable diapers. More particularly, this invention relates to disposable diapers adapted to be secured in place by adhesive tabs.

Disposable diapers provide substantial advantages in convenience over conventional diapers and commonly have a generally quadrilateral configuration with straight or curvilinear longitudinal edges. Disposable diapers are conveniently secured about an infant by means of adhesive tape tabs which are affixed to the diaper along a longitudinal edge thereof, thus eliminating the need for extraneous fasteners, such as pins. In order to protect the adhesive surfaces of the tape tabs, usually a release sheet is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,776,234 to Hoey proposes to fold the tab over on itself at the diaper's edge and do adhesively attach a portion of the folded-over tab segment to the inside surface of the diaper in order to keep the tab from interfering with the manufacturing machinery and with the folding and packaging operations. This requires that the edge of the diaper backing sheet be folded over to present an attachment surface at the front or inside face of the diaper and a relatively involved tab design is necessary for this purpose. Also, undesirable tearing of the diaper facing fabric may result if such a tab is adhesively attached to the facing fabric of the diaper.

While one of the most convenient adhesive systems that has been developed to date is one in which adhesive tabs are adhered to the backing sheet extending outwardly from opposite sides of the diaper at one end thereof and in which the exposed tacky areas of the adhesive strips are provided with readily separable cover strips which protect the exposed areas until ready for use, such adhesive closure systems have the disadvantage that the consumer has to dispose of the cover strips when they are separated from the adhesive tabs. This is an inconvenience to the consumer who is placing the diaper on a baby at about the same time.

U.S. Pat. No. 3,646,937 to Gellert shows a fastening tab which is provided with a release surface folded around an edge of the diaper and permanently bonded to the inside surface of the diaper. A secondary securement means is used to hold the tab on the release surface. SUch an arrangement is disadvantageous because relatively complex manufacturing manipulations would be required to fabricate such a tab.

SUMMARY OF THE INVENTION

The present invention contemplates a diaper having an adhesive tab-type fastener which does not require a separate release sheet to protect the adhesive surface thereof. The disposable diaper embodying the present invention comprises a thin, flexible backing sheet of substantially moisture-impermeable material which forms an outside surface for direction away from an infant, a moisture-retaining layer including a pad or absorbent material which is superposed on the backing sheet and attached thereto, and a fastening tab means carried on the backing sheet and which includes a fixed end attached to the backing sheet and a free working end. An outwardly-facing release region is situated on the backing sheet between the fixed end and a longitudinal margin of the diaper. The free tab end is removably attached thereto. The innermost boundary of the release region forms an acute angle with the longitudinal margin of the diaper and facilitates the initiation of a corner fold for the diaper which exposes a tacky surface on the free working end when the tab fastener is prepared for use.

BRIEF DESCRIPTION OF THE DRAWING

In the drawing,

FIG. 1 is a fragmentary plan view of a disposable diaper embodying the present invention;

FIG. 2 is a sectional elevation taken along plane 2—2 in FIG. 1;

FIG. 3 is a broken plan view showing a disposable diaper having one fastener prepared for use; and FIG. 4 is a perspective view of a disposable diaper embodying the present invention shown in a configuration assumed by the diaper when placed about an infant.

DESCRIPTION OF THE PREFERRED EMBODIMENTS

Referring to FIGS. 1, 2 and 3, disposable diaper 10, having a substantially quadrilateral configuration and presenting inside surface 11 for direction toward an infant and outside surface 12 for direction away from the infant is provided with adhesive tabs 13 and 14 which can be made of polyethylene sheet, polypropylene sheet, or similar materials. As illustrated by tab 13, the tab fastening means comprises fixed end 15 and free working end 16. Similarly, tab 14 is provided with fixed end 17 and free working end 18. Tabs 13 and 14 are attached to diaper 10 by securing fixed ends 15 and 17 to diaper backing sheet 19. The moisture-retaining layer of diaper 10 comprises liquid-pervious facing sheet 20 and absorbent pad 21 which is situated between facing sheet 20 and backing sheet 19.

Fixed end 15 is attached to backing sheet 19 at an attachment zone on outside surface 12 of backing sheet 19 near longitudinal margin 23 by means of pressure-sensitive adhesive layer 22 provided on one side of tab fastener 13. Alternatively, in instances where the tab fastener and the backing sheet both are made of thermoplastic material, fixed end 15 can be secured to backing sheet 19 by heat bonding, and adhesive layer 22 is coextensive only with free working end 16 in such an instance. Outwardly-facing release region 24, usually in the form of a tape segment having an appropriate release coating, e.g., a silicone rubber coating, on the exposed surface thereof is bonded to backing sheet 19 between fixed end 15 and longitudinal margin 23, and free working end 16 is releasably attached thereto. Innermost boundary 25 of release region 24, adjacent to the attachment zone for fixed end 15, is a straight line which forms an acute angle with longitudinal margin 23. Inasmuch as release region 24 is relatively stiffer than backing sheet 19, boundary 25 aids in initiating a corner fold in diaper 10 as shown in FIG. 3 when free end 16 is prepared for use exposing pressure-sensitive adhesive layer 22. Similarly, innermost boundary 27 of release region 26 for free working end 18 is situated along fold line 28 and facilitates the initiation of a fold for exposing a tacky surface on free working end 18. Boundaries 25 and 27 on respective release regions 24 and 26 preferably are situated to form an angle of about 30 to about 45 degrees with the respective longitudinal margins of diaper 10. If desired, release regions 24 and 26 can be formed by printing the appropriate areas on backing sheet 19 with a release coating. Preferably, the areas of release regions 24 and 26 are greater than the respective tacky areas of free working ends 16 and 18 in order to allow for manufacturing tolerances in affixing tab fasteners 13 and 14 to diaper backing sheet 19.

A suitable backing sheet for the diaper embodying the present invention can be an opaque polyethylene web about 0.001 inch thick. Another suitable sheet material for this purpose is a polyethylene terephthalate web having a thickness of about 0.0005 inch.

Several different types of facing materials may be used for diaper facing sheet 20. For example, facing sheet 20 may be made up of a mixture of fibers consisting predominantly of inexpensive short cellulosic fibers, such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$, is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings in commonly assigned U.S. Pat. Nos. 2,862,251; 3,081,514; and 3,081,515. Briefly, such fabrics are foraminous structures wherein groups or groupings of fibers have been arranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers or blends thereof. Typical facing layers made of a polyester-type material can have a weight of ¾ oz./yd.$^2$.

In addition, facing sheet 20 can be formed of a non-apertured material, such as a nonwoven isotropic web, sponge, or the like. In all of the aforementioned facings, the materials should be relatively hydrophobic so as to retard wicking within the facing layer.

Highly moisture-absorbent fibrous pad or batt 21 which is substantially rectangular in shape, but smaller than the facing and backing sheet, is centrally disposed therebetween. Pad 21 can be formed in accordance with the teachings of U.S. Pat. No. 3,612,055 to Mesek et al. Alternatively, a higher moisture-absorbent layer can be provided substantially coextensive with backing sheet 19 if desired.

Typical disposable diapers which can be fitted with a tab-type fastener described hereinabove are shown in U.S. Pat. No. 3,612,055 to Mesek et al. and in U.S. Pat. No. 3,683,916 to Mesek et al. Other suitable disposable diaper structures are shown in U.S. Pat. No. Re. 26,151 to Duncan et al.

Release properties to regions 24 and 26 can be imparted by coating the exposed surfaces thereof with a silicone rubber compound, or the like, or by affixing a sheet of suitable release paper or a tape segment having a suitable release surface to backing sheet 19.

Pressure-sensitive adhesive layers, such as layer 22, are provided by applying a pressure-sensitive adhesive known in the art. The applied adhesive shall have good tack, good cohesive strength, good resistance to moisture and good resistance to aging. Illustrative of such adhesives are mixtures of natural or synthetic rubber, zinc oxide, and various resins, also latices of natural or synthetic rubber, or water dispersions of acrylic tacky polymers or copolymers.

In use, a diaper equipped with the fasteners of this invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing corners 29 and 30 of the underlying end of the diaper into an overlapping relationship with the aforementioned corners so that the diaper snugly encircles the infant's waist. The overlapping corners, i.e., corners 29 and 30 in FIGS. 3 and 4, are then folded back, peeling the corresponding release surfaces from free working ends 16 and 18 which are then adhesively fixed in a desired position on backing sheet 19 of the abdomen-covering end by simply urging the respective pressure-sensitive adhesive surfaces in contact therewith.

The foregoing description and the drawing are illustrative but are not to be taken as limiting. Still other varistions and modifications are possible without departing from the spirit and scope of the present invention.

I claim:

1. A disposable diaper having an inside surface for direction toward an infant when the diaper is worn by that infant and an outside surface for direction away from said infant and including a thin, flexible backing sheet of substantially moisture-impermeable material, a moisture-retaining layer having a pad of absorbent material superposed on said backing sheet and attached thereto, and a fastening tab means positioned solely on the outside surface of said diaper and comprising a fixed end and a free working end; said fixed end being attached to the backing sheet on the outside surface of said diaper at an attachment zone near a longitudinal margin of said diaper, said backing sheet being provided with an outwardly-facing release region adjacent to the attachment zone and between the longitudinal margin of said diaper and the attachment zone, said free working end having a layer of pressure-sensitive adhesive for removable attachment to said release region prior to use, and said outwardly-facing release region having a boundary adjacent to said attachment zone which boundary forms an acute angle with the longitudinal margin of the diaper defining a means for folding back a corner of said diaper bearing said release region to expose said adhesive layer on said free working end for attachment to the outside surface of the diaper when the diaper is applied to the infant.

2. The disposable diaper in accordance with claim 1 wherein the area of said release region is greater than the area of said pressure-sensitive adhesive layer on said free working end.

3. The disposable diaper in accordance with claim 1 wherein the acute angle formed by said boundary is about 30 to about 45°.

* * * * *